United States Patent [19]

Turner

[11] 4,341,227
[45] Jul. 27, 1982

[54] SYSTEM FOR IRRADIATING LIVING TISSUE OR SIMULATIONS THEREOF

[75] Inventor: Paul F. Turner, North Salt Lake, Utah

[73] Assignee: BSD Corporation, Salt Lake City, Utah

[21] Appl. No.: 48,515

[22] Filed: Jun. 14, 1979

Related U.S. Application Data

[63] Continuation-in-part of Ser. No. 2,583, Jan. 11, 1979, abandoned.

[51] Int. Cl.³ ............................................. A61N 1/40
[52] U.S. Cl. ................................................... 128/804
[58] Field of Search ......................................... 128/804

[56] References Cited

U.S. PATENT DOCUMENTS

| | | | |
|---|---|---|---|
| 2,220,269 | 11/1940 | Patzold et al. | 128/804 |
| 2,242,886 | 5/1941 | Hirschland et al. | 128/804 |
| 2,404,283 | 7/1946 | Gieringer | 128/804 |
| 2,407,690 | 9/1946 | Southworth | 128/804 |
| 3,077,195 | 2/1963 | Folsche | 128/804 |
| 4,108,147 | 8/1978 | Kantor | 128/804 |
| 4,140,130 | 2/1979 | Storm | 128/804 |

FOREIGN PATENT DOCUMENTS

| | | | |
|---|---|---|---|
| 2348050 | 4/1975 | Fed. Rep. of Germany | 128/804 |
| 862646 | 3/1961 | United Kingdom | 128/804 |

*Primary Examiner*—William E. Kamm
*Attorney, Agent, or Firm*—Hubbard, Thurman, Turner, Tucker & Glaser

[57] ABSTRACT

Disclosed is a system for irradiating living bodies, or portions thereof, using electromagnetic radiation (EMR). A source or generator provides electromagnetic energy at a selected frequency, within an operational band width, via a coaxial cable to an applicator for radiation into living tissue. The source, cable, and applicator each have a characteristic impedance approximately equal to the average impedance of the living tissue over a broad frequency band, thus enabling efficient operation of the apparatus without using auxiliary impedance matching devices. The applicator is of a waveguide transmission line type enabling efficient transmission and radiation of the electromagnetic energy and further incorporates means for cooling surface portions of the living tissue during radiation thereof. Selective dielectric loading of the applicator enables shaping of the radiated power to a preselected distribution. A feedback control system including temperature sensors placed onto and into the tissue enables the control of tissue surface and sub-surface temperatures within a preselected range by adjusting the power level of the generator.

14 Claims, 15 Drawing Figures

SYSTEM FOR IRRADIATING LIVING TISSUE OR SIMULATIONS THEREOF

CROSS-REFERENCE TO RELATED APPLICATION

This application is a continuation-in-part of U.S. Patent Application Ser. No. 2,583 filed Jan. 11, 1979, now abandoned.

The present invention relates generally to irradiating human or animal tissue, and more particularly to electromagnetic radiation (EMR) apparatus for such irradiation, for example, to produce hyperthermia within living bodies, or portions thereof.

It has been long known that electromagnetic energy at frequencies greater than about 10 KHz produces heating in living tissue. In fact, many years ago the word "diathermia" was used to describe the heating of human tissue by high frequency electrical currents.

Such heating may have many beneficial uses, such as, for example, the warming of selected tissue after hypothermal surgery, the enhancement of blood circulation, and the necrosis of selected tissue such as tumors and malignant growths.

With regard to the latter, it is generally known that death, or necrosis, of living tissue cells occurs at temperatures elevated above the normal cell temperature and that the death rate of the tissue is a function of both the temperature to which it is heated and the duration for which the tissue is held at such temperature.

It has been reported that some types of malignant cells can apparently be necrotized by heating them to a temperature which is slightly below that temperature injurious to most normal cells. In addition, some types of malignant cells may be selectively heated and necrotized by hyperthermia techniques because masses of these malignant cells typically have considerably poorer blood flow heat dissipation properties than does the surrounding normal tissue. As a result, when normal tissue containing such malignant masses is heated by EMR, the resultant temperature of the malignant mass may be substantially above that of surrounding healthy cells.

Although some disagreement exists regarding exact temperatures, most malignant cells have a relatively limited temperature range in which hyperthermia is effective in causing necrosis. Below a threshhold temperature of about 41.5° C. (106.7° F.) insubstantial thermal damage occurs even in those types of malignancies which have a greater sensitivity to temperature than do normal cells. In fact, at temperatures just below this threshhold, growth of some types of malignancies may be stimulated. At temperatures within or above about 43° to 45° C. (109.4° to 113° F.) thermal damage to most normal cells occurs.

Because of the normal cooling and heat transfer properties of a large body, such as a human body, or portions thereof, deeply located malignant growths can seldom be heated to a lethal temperature using surface heating techniques without causing excessive thermal damage to the overlying normal tissues.

An advantage of EMR is that energy incident to a body is not totally absorbed by the surface tissue; rather, a substantial amount of energy penetrates some distance into the body before it is absorbed to cause heating. It is generally known that lower frequency EMR has greater penetration into tissue than higher frequency EMR. For example, in accordance with an article by A. W. Guy, et al, published in Proceedings of the IEEE, Vol. 63, No. 1, January, 1974, entitled "Therapeutic Application of Electromagnetic Power", the depth of penetration in human muscle and fat at 100 MHz is 6.66 cm. (2.62 in.) and 60.4 cm (23.8 in), respectively, while at 915 MHz the depth of penetration is only 3.04 cm (1.2 in) and 17.7 cm (6.97 in) respectively.

A serious problem associated with EMR hyperthermia of a malignant growth located deep within a body, has been causing lethal heating of the malignancy without and damaging a large amount of adjacent healthy tissue or healthy surface tissue layers. Such over heating of normal cells may occur because the applicator used to radiate EMR into the body, emits a distorted energy distribution into the tissue, the applicator is not efficiently coupled with regard to transmission of the EMR, into the body tissue, or surface cooling is not adequate.

That is, the applicator, during EMR, causes certain areas to receive significantly more energy than adjacent areas and as a result such areas become "hot spots".

This problem is further complicated when the EMR frequency is below 1 gigahertz. In general, the lower the EMR frequency, the larger the applicator must be in order to effectively carry and radiate electromagnetic energy into tissue and, as a result, applicators for efficiently irradiating electromagnetic energy below 1 gigahertz tend to be large in size and cumbersome to handle. In addition, such applicators emit low frequency EMR in a large radiation pattern which is not suitable for heating small masses of malignant tissue located well beneath surface layers of the body being irradiated.

It is well known that waveguide transmission lines can efficiently conduct or transmit electromagnetic energy. Such waveguides, however, useful for carrying electromagnetic energy in the frequency range below 1 gigahertz are also generally large and cumbersome, unless they are dielectrically loaded, or filled, with a dielectric material having a dielectric constant substantially greater than unity.

Early attempts, such as, for example, disclosed by G. C. Southworth in U.S. Pat. No. 2,407,690, issued on Sept. 17, 1946, to utilize a dielectrically loaded waveguide as an electromagnetic applicator in an electrotherapeutic system, only recognize the principle of loading a waveguide to reduce the size thereof, without solving the problems of producing "hot spots" as hereinabove referenced. Further, such applicators are limited in operation to a single or limited frequency range and require extensive tuning apparatus. Hence, they are not suitable for heating tissue at different depths within the body.

Although lower frequency EMR has greater penetration into a body, the surface areas are also heated, and during extended application of EMR may become hot enough to damage surface tissue. In order to efficiently couple the energy radiated from the applicator into the body tissue it is necessary to position the applicator in contact with, or very close to, the body surface. Hence, a conventional applicator placed in direct contact with surface tissue or immediately adjacent thereto interferes with access to such surface areas to enable cooling thereof by auxiliary apparatus.

G. Kantor, in U.S. Pat. No. 4,108,147 issued on Aug. 22, 1978 recognized that the coupling of electromagnetic energy into body tissue enhanced by utilizing an applicator adapted for direct contact with tissue to be irradiated. Further, the applicator disclosed by Kantor is of a dielectrically loaded waveguide type, in order to provide a more uniform heating pattern than a spaced applicator.

However, Kantor does not address the problem of efficiently coupling electromagnetic energy from a source, into living tissue, nor the problem of cooling surface layers thereof.

The problems of low efficiency and inflexibility of hyperthermia apparatus are common with generally available diathermy systems. Such apparatus has heretofore typically included arrangements of standard EMR components, and as a consequence of using "off-the-shelf" components, mismatch of characteristic impedances ($Z_o$) at various interfaces and interconnections has frequenly limited EMR hyperthermia system efficiencies.

Component mismatch has many times been ignored or been compensated for by "tuners" and "line stretchers" positioned at calculated distances between an EMR generator and the mismatching interface. These devices may be adequate when only a single EMR frequency or a very narrow range of EMR frequencies is needed in the system. However, to irradiate selected tissue located at different depths within the body and over different areas, capability for varying applied EMR frequencies over a range of frequencies is necessary. Further, such compensating "tuners" and "line stretchers" create standing waves within the EMR apparatus which results ultimately in unwanted heating of connecting cable, decreasing efficiency and increasing leakage radiation. As a result of these and other problems, safe, efficient and relatively simple low frequency (below 1 gigahertz) EMR hyperthermia apparatus have not heretofore been generally available.

The present invention provides EMR hyperthermia apparatus which efficiently couples electromagnetic irradiation into tissue at a selected frequency, throughout a relatively broad frequency range, without the necessity of auxiliary impedance matching apparatus. Included, in the invention are highly efficient EMR applicators capable of uniformly and efficiently heating deep portions of a body using EMR frequencies below 1 gigahertz while cooling surface portions of the body.

A system for radiating living tissue or simulations thereof, in accordance with the invention, comprises an electromagnetic radiation source having an output impedance substantially equal to an average characteristic impedance of a waveguide-type transmission line applicator adapted for radiating electromagnetic energy into the tissue. The applicator includes a dielectric disposed partially filling the transmission line and in operative relationship therewith which enables the applicator characteristic impedance, when radiating into tissue to be approximately equal to an average characteristic impedance of living tissue or simulations thereof, at a selected frequency. Interconnecting the applicator and the electromagnetic radiation source are transmission means having a characteristic impedance substantially equal to the average characteristic impedance at the selected frequency.

Since the electromagnetic radiation source, the applicator and the transmission means all have approximately the same characteristic impedance and these characteristic impedances are approximately equal to the average characteristic impedance of the living tissue, substantially no reflection of EMR occurs at interfaces therebetween, because of impedance mismatch, and as a consequence the apparatus efficiently couples electromagnetic radiation from the source into the body without appreciable energy loss.

In an exemplary embodiment of the invention, the radiation source is of a variable frequency type and has an output impedance substantially equal to an average characteristic impedance of tissue, or simulations thereof over a selected frequency range having a band width ratio in excess of 50%.

A dielectric medium, in operative relationship with the waveguide-type transmission line, enables the applicator to have a characteristic impedance, when radiating into the tissue approximately equal to the average characteristic impedance throughout the recommended frequency range. Hence the apparatus is able to efficiently couple EMR into tissue at any frequency within the applicator's band width without the need for auxiliary apparatus, such as "stub tuners" which would require adjustment upon changing from one frequency to another.

By incorporating cooling means within the applicator the apparatus can cool surface areas despite the fact that the applicator is placed in contact with or adjacent to the tissue for efficient energy coupling thereinto.

A feedback control system, in operative relationship with the electromagnetic radiation source and including at least one temperature sensor disposed in said living tissue, or simulation thereof, acts to limit the temperature of monitored portions of the living tissue by controlling the output of the radiation source.

Additionally, the invention includes waveguide-type applicators for use in the system, or separately, which include a waveguide-type transmission line, dielectric means partially filling the transmission line, and disposed in operative relationship therewith for enabling the transmission line to have a characteristic impedance, when radiating electromagnetic energy into the tissue, approximately equal to an average characteristic impedance of the living tissue, or simulations thereof, at a selected frequency, and coupling means adapted for receiving electromagnetic energy from a conductor and for launching the electromagnetic energy into the waveguide-type transmission means.

In one embodiment of the invention an applicator includes a generally rectangular waveguide-type transmission line having sidewalls with interconnecting top and bottom portions. The dielectric is disposed within the transmission line and along the sidewalls thereof and, in addition to enabling the applicator to have a preselected characteristic impedance, it also causes the transmission line to irradiate electromagnetic energy in a preselected energy distribution into living tissue.

A coupler is included for receiving electromagnetic energy from a coaxial-type conductor and for launching the electromagnetic energy into the waveguide transmission line. The coupler has portions thereof which are disposed within the transmission line and in operative relation with the dielectric for launching the electromagnetic energy into the transmission line without substantial electromagnetic energy reflected into the coaxial conductor. These features further enables the use of the applicator with a coaxial cable without energy loss in the form of electromagnetic energy reflections along the coaxial conductor and back into the radiation source which may either damage the source, result in undue heating of the coaxial conductor, or cause radiation leakage which may be hazardous to operating personnel.

A blower is incorporated into the applicator for forcing cooling air through an air passage through the dielectric and out an electromagnetic energy radiating end of the transmission line. Since the applicator is positioned adjacent the surface of the tissue during radiation of tissue, air emitted from the transmission line flows across the surface portions of the living tissue to cause cooling thereof.

In another embodiment of the invention an applicator includes a waveguide-type transmission line having a central portion and adjoining open side portions with the dielectric being disposed within the central portion of the transmission line.

A further embodiment of the invention includes an applicator for irradiating electromagnetic energy into living tissue, or simulations thereof, having a waveguide-type transmission line, first dielectric means, and second dielectric means. The first and second dielectric means are disposed in operative relationship with the transmission line for enabling the transmission line to have a characteristic impedance, when radiating electromagnetic energy into the tissue, approximately equal to an average characteristic impedance of the living tissue, or simulations thereof, at a selected frequency.

Coupling means are provided for receiving electromagnetic energy from a coaxial type conductor and for launching the electromagnetic energy into the waveguide-type transmission line without substantial electromagnetic energy reflection into the coaxial conductor throughout said frequency range.

In addition, the second dielectric means includes a fluid dielectric and a compartment for containing the fluid, said compartment being disposed within the transmission line adjacent one end thereof. The compartment includes a wall forming an applicator radiating surface and fluid inlet and outlet means for enabling the fluid dielectric to be circulated through the compartment, thereby enabling the second dielectric means to act as a cooling medium for cooling surface portions of living tissue during irradiation thereof by the applicator when the tissue is held against the applicator radiating surface.

Other advantages and features of the invention will appear from the following description when considered in connection with the accompanying drawings, in which:

Figure 1:
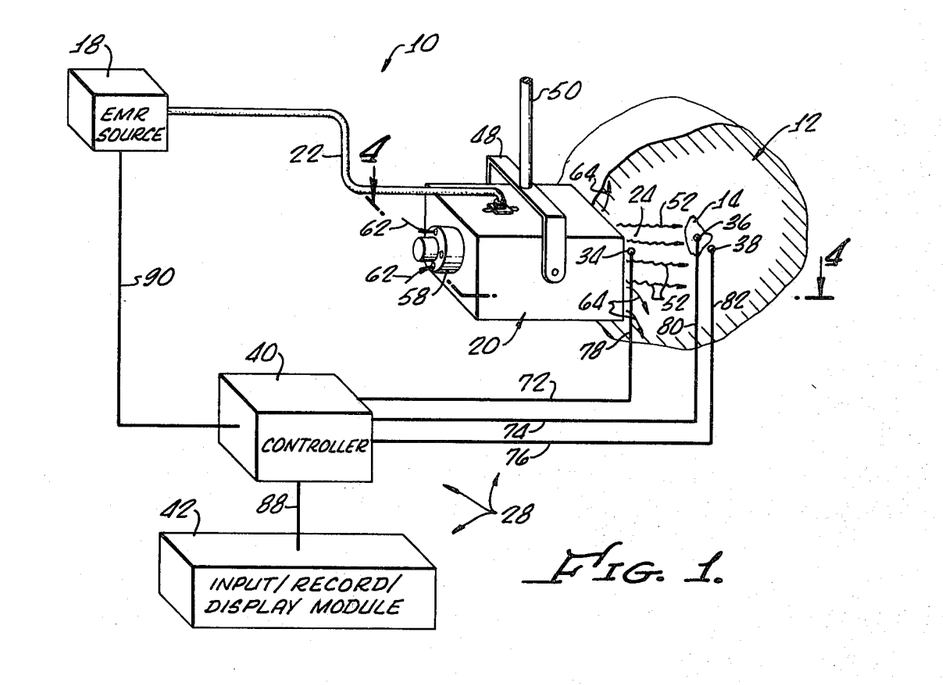
FIG. 1 is a representation, partially in perspective and partially in block diagram form, of an exemplary embodiment of a system for irradiating living tissue, or simulations thereof and generally showing a waveguide-type transmission line applicator, electromagnetic energy source, a coaxial cable for transmitting electromagnetic energy therebetween, and a feedback system which includes temperature sensors, a controller and a record/display module.

Referring now to FIG. 1, a system 10 for irradiating living tissue 12 or simulations thereof, including a malignant mass 14, generally includes an electromagnetic radiation generator or source 18, an applicator 20 and a coaxial cable 22 for transmitting electromagnetic energy between the source and the applicator. It should be appreciated that a waveguide type transmission line could be employed to conduct electromagnetic energy between the source 18 and the applicator 20, however, the coaxial cable is preferred because it permits greater flexibility in movement of the applicator.

In order to control or hold the temperature of the irradiated tissue 12, the malignant mass 14 and surface portions, or layers, 24 of the tissue, within a preselected range, the system 10 includes a feedback control system 28 including temperature sensors 34, 36, 38, a controller 40 and an input/record/display module 42. Hereinafter, reference may be made only to tissue, however, it should be understood that such reference is meant to include both living tissue and simulations thereof.

In operation, the applicator 20 is held immediately adjacent the tissue surface 12 by a bracket 48 and a supporting arm 50. Electromagnetic energy is fed from the source 18 via the cable 22 into the applicator 20 and thereafter radiated into the tissue, as indicated by the arrows 52, towards the malignant mass 14 located within the tissue.

It is important that the applicator be placed in contact with, or immediately adjacent to the tissue to be irradiated in order to achieve proper coupling of the radiated energy thereinto. At frequencies approaching 1 gigahertz, a significant amount of energy may be absorbed by the tissue surface 24 causing heating thereof to a temperature exceeding 43° C. unless otherwise cooled.

A feature of the present system 10 is that the applicator 20 includes means for cooling of the surface tissue 24 during radiation thereof, using forced air or liquid, and importantly directing such cooling onto the irradiated area.

As will be discussed hereinafter in greater particularity, the applicator generally includes a blower 58 for forcing air through the applicator and across the surface portions as represented by the arrows 62, indicating inlet air, and arrows 64, indicating the outlet air flowing over the tissue surface 24.

The temperature sensor shown at 34 is representative of one or a plurality of sensors disposed at or just below the surface layer 24, a single sensor being shown for clarity. Similarly, the sensors shown at 36 and 38 respectively represent one or a plurality of sensors disposed in, and adjacent to, respectively, the malignant mass 14.

It is to be appreciated that such sensors should be of a type which does not interfere or absorb electromagnetic energy, otherwise correct tissue temperatures will not be ascertained. Such sensors may be of a thermister type utilizing carbon-impregnated plastic leads, optical type with connecting optical fibers, or a liquid crystal type as generally described by Cetas, T. C. in *PROCEEDINGS OF THE INTERNATION CONFERENCE ON CANCER THERAPY, HYPERTHERMIA AND RADIATION,* Apr. 28-30, 1975, Washington, D.C. (Am. Coll. of Radiology, Chevy Chase, Md.).

The temperature sensors 34, 36, 38 are connected to the controller 40 via lines 72, 74, 76 respectively, connected to sensor lead portions 78, 80, 82 which are sufficiently long enough to extend beyond the radiation field 52 of the applicator. Such leads are customarily provided with the temperature sensors.

The controller 40 includes computing portions, not shown, for receiving signals from the temperature sensors 34, 36, 38 and comparing such signals with predetermined signals corresponding to preselected or set temperature levels as inputed to the controller 40 via module 42 through a connecting line 88. The controller 40 may operate in a comparator like manner to control the output of the source 18 to the applicator 40 via the interconnecting line 90. For example, when the temperature of any of the temperature sensors 34, 36, 38 reaches a set temperature level, the controller will act to either reduce the power output of the source 18, or shut it off entirely, until the temperature, as indicated by the sensors, falls below the set temperature level.

The module 42 may include recording and output facilities, such as a printer/plotter and CRT monitor, not shown, so that the entire time-temperature relationship of the tissue 12 as indicated by the sensors 34, 36, 38, can be monitored during irradiation.

It is important to note that the system 10 does not require impedance matching devices, such as "stub tuners" or "line stretchers" to operate efficiently. However, such a tuner would provide some small improvement in efficiency and reduction in reflected power. The source 18, cable 22 and applicator 20 each have a characteristic impedance substantially equal to the average characteristic impedance of the tissue over the range of frequency to be radiated into the tissue. Hence, there being little impedance mismatch, efficient conveyance of electromagnetic energy is possible without auxiliary matching devices. However, since different bodies have various fat layers and moisture content, a tuning device would still further increase efficiency and reduce reflected power.

More specifically, for animal tissue 12, the average characteristic impedance is, in part, a function of (1) the frequency of the electromagnetic field set up therein, (2) the specific content of the tissue, namely, bone, fat, or muscle; and (3) the temperature of the tissue. For the frequency range between 50 megahertz and 1 gigahertz, an overall average real impedance of animal tissue is approximately 50 ohms.

As will be hereinafter discussed in further detail, the characteristic impedance of the applicator 20, when radiating into animal tissue 12, over a frequency range between approximately 420 to 750 MHz, is close to 50 ohms. The coaxial cable 22 is of a common commercial type having a characteristic impedance of 50 ohms as is the electromagnetic radiation source 18. The source may be of a single frequency type, however, for greater flexibility in experimentation and in varying the depth of penetration of the electromagnetic energy, a variable frequency source is preferred, such as a model 15152 RF power generator manufactured by MCL Inc. (Microwave Components Laboratory), which has a frequency range of 10 megahertz to 2500 megahertz and an output power of approximately 100 watts, with various plug-ins.

Figure 2:
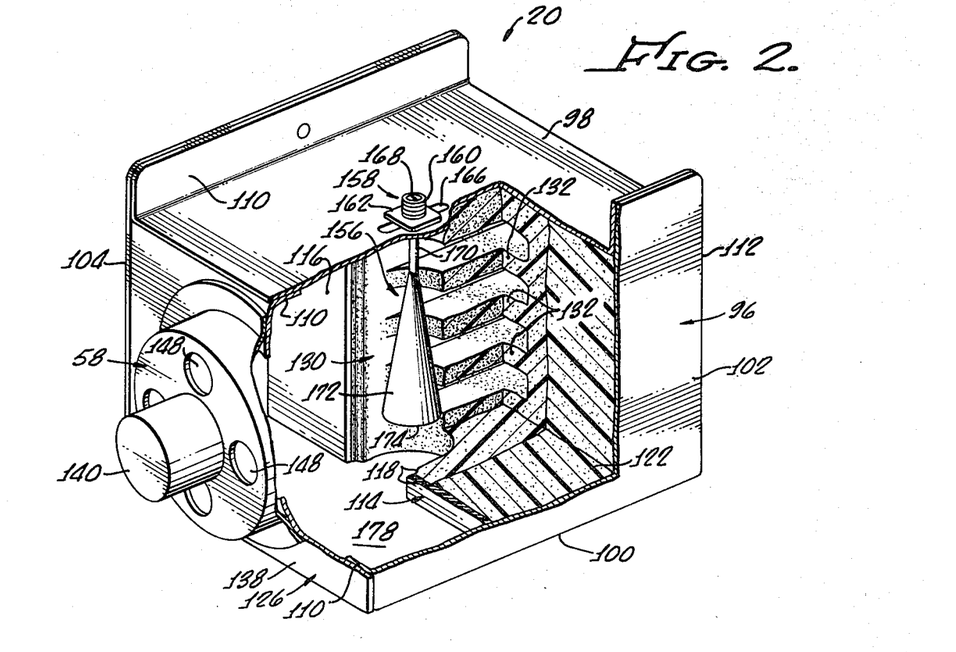
FIG. 2 is an enlarged perspective view of the waveguide-type transmission line applicator, partially broken away to show dielectric compartments within the waveguide, a ribbed filler therebetween, and a coupler for receiving electromagnetic energy from the cable and for launching received electromagnetic energy into the waveguide.

Referring now to FIG. 2, the applicator 20 for use with the radiation apparatus 10 includes a generally retangular waveguide-type transmission line 96 having a top and bottom 98, 100 with inner connecting sidewalls 102, 104. The top, bottom and sidewalls of the waveguide 96 are formed of sheet metal material having flanges 110 thereon suitable for bonding to adjacent top, bottom or sidewall portions by means of welding, or other means, not shown, to form a generally rectangular waveguide 96 having general overall dimensions of approximately eight (8) inches in length, six and two thirds ($6\frac{2}{3}$) inches in width and four (4) inches in height.

The waveguide-type structure of the applicator permits more efficient transfer of electromagnetic energy therethrough than many other types of applicators hereinbefore used, such as parabolic reflectors, paddles or the like, over a wide operational bandwidth.

In general, the overall dimensions of the waveguide-type transmission line are dependent upon the frequency of the energy to be radiated thereby. The applicator 20 is representative of a class of applicators which may be constructed in which an applicator designed for higher frequencies would be proportionately smaller and one designed for lower frequencies would be proportionately larger than the applicator 20, which has an operational range of between 420 MHz and 750 MHz. Determination of the applicator dimensions is generally experimental using certain theoretical guidelines as will be presented in a later section.

Figure 3:
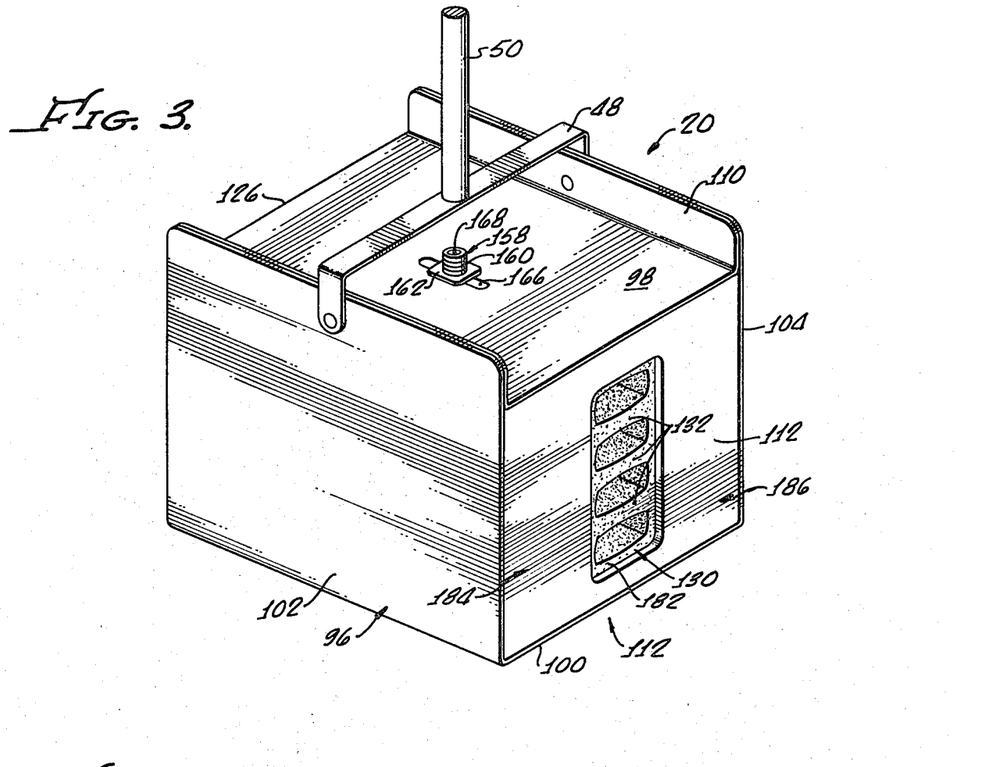
FIG. 3 is an overall perspective view of the waveguide-type transmission line applicator showing an EMR emitting end, or face thereon and an end surface of the ribbed filler.

To provide a shaped energy distribution across an EMR emitting end or face 112, see also FIG. 3, the waveguide-type transmission line 96 is dielectrically loaded along the sidewalls 102, 104 thereof. As will be henceforth discussed, this dielectric loading also enables the applicator to be smaller in dimensions than a totally air filled waveguide, and in part enables the applicator to have a characteristic impedance approximately equal to 50 ohms over the frequency of 420–750 MHz.

In the way of definition, "dielectric loading" means the use of a dielectric medium in or about a waveguide which alters the electric field therein. A dielectric medium is a non-conducting material having the property that the energy required to establish an electric field therein is recoverable, in whole or in part as electric energy. For reference purposes the dielectric constant of air is 1.0.

The dielectric loading in the applicator 20 includes two generally rectangular sidewalls or compartments 114, 116 having thin walls 118, 120 (see also FIG. 4) of a relatively low dielectric constant material such as Plexiglas, which are filled with a dielectric medium 122 having a relatively high dielectric constant of approximately 12. As shown, the dielectrically loaded compartments 114, 116 extend between the waveguide top 98 and bottom 100 from the emitting end 112 to a predetermined distance d, from a waveguide rearward end 126. As will be hereinafter discussed, the placement of the dielectrically loaded compartments within the waveguide 96 enhances the operational frequency bandwidth of the applicator 20.

While the dielectric medium may be in any form, in this instance the dielectric medium 122 is a powder known as Eccoflex HiK adjusted dielectric pack-in-place powder available from Emerson & Cummings, Inc.

Use of the dielectric medium as disposed within the waveguide 96, permits the applicator 20 to conduct electromagnetic energy in the frequency range of 420-750 MHz in a relatively small waveguide, namely $6\frac{2}{3}$ inches by 4 inches. For comparative purposes, if a waveguide applicator were constructed without dielectric loading, to efficiently conduct electromagnetic energy in the approximate 420–750 megahertz range, the dimensions of the waveguide would necessarily be approximately 35 inches by 20 inches according to conventional waveguide-type transmission line design. Clearly, an applicator having dimensions of this magnitude would be inappropriate for use in selectively heating portions of living tissue within most bodies. Hence, it can be seen that the dielectric loading permits the applicator to conduct electromagnetic energy in this frequency range while maintaining a usable radiating face 112 of approximately four (4) inches by a six and two-thirds ($6\frac{2}{3}$) inches.

The dielectric filled compartments 114, 116 are supported and held in a spaced apart relationship by a low dielectric filler 130 having a set of spaced apart ribs 132 formed therein. Formed of a low dielectric (approximately 1.2) foam material, also available from Emerson & Cummings, Inc., the filler acts electrically as air. If another form of dielectric medium or manner of constructing the compartments is employed, the filler 130 may be modified or eliminated altogether.

It is important, however, that the central portion of the waveguide 96 be air filled, or with a medium having a dielectric constant approximately equal to air in order that the applicator emits energy in a preselected shaped distribution. The exact dimensions of the compartments 114, 116 and the filler 130 therebetween are found experimentally using theoretical guidelines as will be presented in a later section.

Additionally, it is important that the filler 130, or space between the compartments, be open if air cooling of the surface tissue 24 is provided. It is to be appreciated that if liquid cooling is used the filler 130 may not be open to the flow of air.

As previously discussed, the higher the radiation frequency, the less penetration of the electromagnetic energy into tissue. In other words, a greater proportion of the energy is deposited at or near the surface layers of the tissue. Consequently for the applicator 20 operating at the higher end of its range, namely near 750 MHz, it is an important feature that the surface layers of the tissue can be cooled to prevent overheating and hence, unwanted necrosis of skin or surface tissue.

Figure 4:
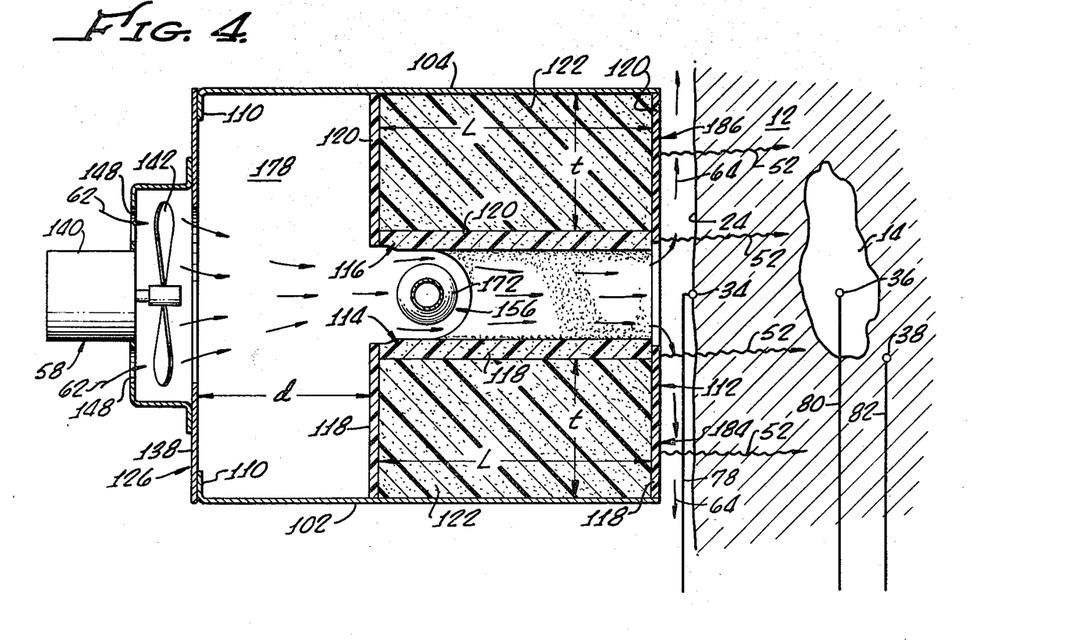
FIG. 4 is a cutaway plan view of the applicator of FIG. 3, showing the disposition of dielectric within the waveguide, the position of the coupler with respect to the dielectric and waveguide, and a blower disposed on a rear end of the wave guide applicator for forcing air therethrough to cool surface areas of tissue when the waveguide applicator is positioned in operative relationship therewith; also shown is a representation of a temperature sensor disposed at a surface position on the tissue sample and a representation of air flow through the applicator and over the tissue sample.

As shown in FIGS. 2 and 4, the air blower 58 is mounted to a mounting plate 138 attached to the rearward end 126 applicator which includes an electrical motor 140 for driving a fan blade 142. In operation, air is drawn in through inlet ports 148 and forced through the ribbed filler 130 of the applicator. The air flow, as indicated by the arrows 64, passes over surface portions 24 of the tissue 12 causing cooling thereof by convection.

It should be appreciated that while room temperature air may be used for cooling, refrigeration coils, or a remote air cooler, not shown, could be incorporated to provide colder air. In addition, fluid cooling means utilizing for example, nonmetallic tubes or a liquid bag not shown, to pass a dielectric cooling fluid onto or over the surface portions 24 of the tissue 12 may be incorporated into the applicator 20 to provide a greater cooling capacity. In fact, when the applicator 20 is positioned in contact with the surface 24, fluid cooling would be preferred over air cooling.

Referring again to FIGS. 2 and 3, the applicator 20 includes a launcher or coupler 156 for receiving electromagnetic energy from the coaxial conductor 22, not shown in FIG. 2 or 3, and for launching the electromagnetic energy into the transmission line applicator 20. The coupler 156 includes a standard coaxial connector 158 having an outer threaded portion 160 adapted for connection to the coaxial conductor 22, and a base portion 162, slidably mounted in a slot 166 in the waveguide top 98. This mounting arrangement allows factory adjustment of the coupler 156 within the applicator 20 in order to maximize coupling between the cable 22 and the applicator and substantially eliminate energy reflection into the cable. It should be appreciated that once the optimum position of the coupler 156 is determined, as will be hereinafter discussed, the coupler position is no longer adjusted.

A center conductor 168 of the coaxial connector is connected to a rod or tube 170 having a flared or cone-like portion 172 with a flat closed end 174. The cone portion of the coupler 156 and a flat end 174 thereon provides proper capacitance coupling between the center conductor or pin 168 and the waveguide 96 as is well known in the art.

The placement of the coupler 156 with respect to the dielectric compartments 114, 116 and an unloaded or empty portion 178 of the waveguide extending rearward from the compartments 114, 116, enables the operational frequency band width of the applicator to be from approximately 420 to 750 MHz, or a bandwidth ratio of about 60%. Bandwidth ratio is defined herein to mean the ratio of $$\frac{f_2 - f_1}{\sqrt{f_2 f_1}} \times 100\%$$

where $f_1$ and $f_2$ are the lower and upper frequency limits respectively.

A bandwidth in excess of 30% is preferred because it enables the apparatus 10 to vary the depth of penetration of the EMR into the tissue 12 as may be necessary depending on the location of the malignant mass 14. This bandwidth is large compared with the operational bandwidth of conventional dielectrically loaded waveguide applicators. Ordinary dielectrically loaded waveguide techniques would suggest the dielectric extend the entire length of the waveguide and the waveguide is terminated with a shorting plate across the side walls and top and bottom of the waveguide. The shorting plate is usually placed one-quarter wave length away from the launcher, which causes the waveguide to have only about 20 to 30% operational bandwidth ratio, but instead, in accordance with the technique shown by the present invention, dielectric load ends near the coupler 156, causing an air filled section 178 of waveguide 96. This forces energy in the dielectric filled portion because the air filled portion would be in cut off at the frequencies of operation. This is inherently broad band because there is no frequency dependent quarter-wave spacing as needed when a short is used.

The location of the coupler 156, the overall dimensions of the applicator 20 and the placement of the dielectrically loaded compartments 114, 116 therein are determined experimentally as follows:

The length of the dielectrically loaded compartments 114, 116 should be long enough to clearly establish wave propagation therein, of the electromagnetic energy at a frequency of interest. Since lower frequencies have longer wavelengths, the lowest frequency that the waveguide applicator is to be used for is used to determine the compartment length, L.

To establish wave propagation, the length, L, of the compartments 114, 116 should be greater than approximately ⅓ of the wavelength of the electromagnetic energy within the applicator. This wavelength is found experimentally by utilizing a waveguide structure, not shown, having the same height and width of the applicator 20 but with extended side walls having dielectric loaded compartments extending the entire length thereof. Electromagnetic energy at 420 MHz is fed into the waveguide structure and the wavelength is measured. At 420 MHz, the measured wave length is approximately 15 inches, hence the length, L, of the compartments should be approximately 5 inches.

The distance, d, between the compartments 114, 116 and the applicator rearward end 126 is also experimentally determined. Using a waveguide structure, not shown, having five inch long dielectrically loaded compartments and waveguide sidewalls of greater length, a shorting plate, not shown, extending between the sidewalls and the top and bottom of the waveguide structure, is moved toward the compartments while the waveguide is fed by a swept frequency of 100 to 1000 MHz electromagnetic energy and the coupling efficiency is measured between the transmission line and the feeding coaxial line by monitoring reflected power meter. The shorting plate is moved toward the compartment until reflected power is noted to slightly change. This position of the shorting plate indicates the point at which the waveguide can be terminated without affecting coupling efficiency. This distance, d, for the applicator 20 is approximately 3 inches, and hence, an overall length of the applicator of approximately 8 inches.

It should be appreciated that the rear wall 138 of the applicator does not act as a shorting plate or significantly affect the coupling and electrical operation of the application 20, but merely serves as a mounting plate for the blower 58, and reduces stray radiation.

The exact location of the coupler 156 is also determined in an experimental manner by adjusting its position within the slot 166 while measuring the coupling efficiency between the electromagnetic energy source, the coaxial cable and the applicator. The coupling efficiency is determined in a standard manner by measuring the reflected energy from the applicator back towards the source while moving or tuning the coupler 156. The optimum position of the coupler is established when the applicator does not reflect a substantial amount of energy back toward the source via the cable 22. In this manner, the placement of the coupler 156 compensates for any impedance mismatch which may otherwise be caused by the 50 ohms cable 22 being connected to the waveguide. This adjustment is best made while radiating the tissue, and sweeping the frequency.

In operation, the electromagnetic energy in the frequency range of approximately 420 MHz to 750 MHz will be launched into the applicator by the coupler 156 and substantially all of the energy will be conducted by the dielectric filled portion of the guide. Little if any will pass in the direction of the rearward air filled portion 178 to the guide.

Another important aspect of the dielectric compartments 114, 116 is that they are operative with waveguide 96 to shape the electromagnetic energy radiation pattern from the applicator's emitting end 112 (FIG. 3) into a preselected energy distribution.

To obtain uniformity of the electromagnetic field within the air filled or ribbed filler 130, the thickness of the side wall compartments, t, (FIG. 4), is found in accordance with the formula:

$$f_p = \frac{C_o}{4t\sqrt{K-1}}.$$

as discussed by Heren and Baird in IEEE Transactions of Microwave Theory and Techniques, page 884–885, November 1971.

Using a frequency, $f_p$, equal to approximately 420 megahertz, a dielectric constant, k, of 12, and the velocity of light in free space $C_o$, the thickness t is approximately 1.9 inches. The overall height and width of the applicator are adjusted experimentally to cause the characteristic impedance of the applicator to be approximately 50 over the entire operational range of 420 MHz to 750 MHz.

The use of dielectric compartments 114, 116 adjoining the side walls 102, 104 of the waveguide 96 causes the electromagnetic energy radiation from the applicator emitting face 112 to be relatively less from a forward end 182 of the filler 130 than from adjoining areas 184, 186 on the applicator emitting face 112.

The shaping of the energy distribution emitted by the applicator is particularly important within the operational frequency range of 420–750 MHz where the depth of penetration into tissue may only be a few inches and substantial amount of energy is absorbed at or near the surface layers. Because the tissue being irradiated generally has uniform cooling capability, by means of blood flow, there is a tendency for a hot spot to develop in a central region of tissue being irradiated by an applicator at these frequencies.

Figure 5:
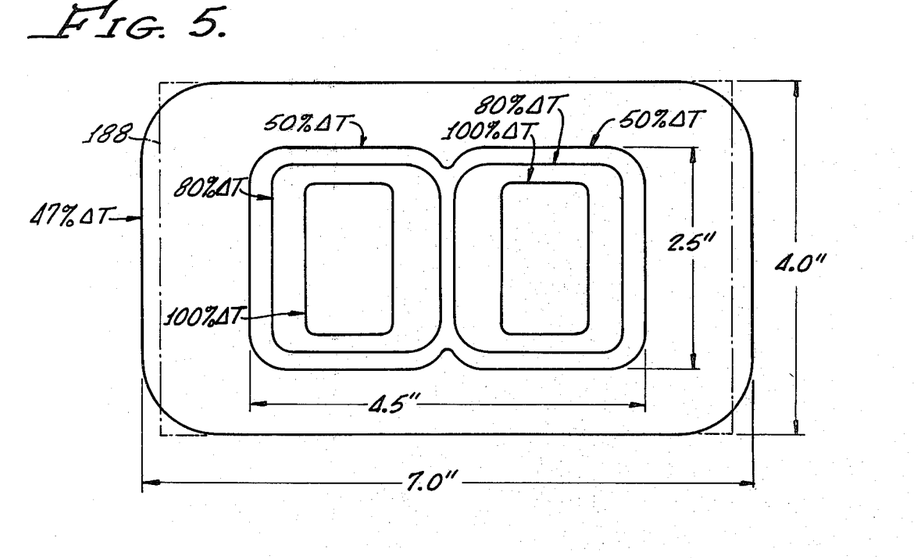
FIG. 5 is a plot of a temperature distribution or heating pattern at the surface of a simulated tissue sample after irradiation thereof with the applicator shown in FIG. 3; an outline of emitting end of the applicator is indicated to show the relative shape of the heating pattern with respect thereto.

FIG. 5 illustrates the general shape of the heating pattern in simulated, or phantom, tissue sample for the applicator 20 while irradiating electromagnetic energy at the frequency of approximately 420 MHz, without cooling of the surface. Plotted is the percent temperature change near the surface relative to the greatest temperature change indicated as one hundred percent. Actual temperature measurements were taken at 0.6 cm. below the surface. Isothermal lines are drawn for surface temperatures being 80 percent of the maximum temperature change, 50 percent of the maximum temperature change and 44 percent of the maximum temperature change. The overall height and width of the applicator emitting face 112 is indicated by a broken line 188.

The simulated tissue has a dielectric constant of approximately 50 ohms over the frequency range of interest and is composed of approximately 75.4% water, 0.9% NaCL, 15.2% polyethylene powder and 8.5% Superstuff. The Superstuff is a material available from WHAMO Manufacturing Co. As shown, the heating pattern resulted from radiating the simulated tissue with approximately 50 watts of electromagnetic energy for less than 20 minutes.

Thus, the side loaded waveguide-type applicator 20 enables more energy to be coupled into tissue at 420–750 MHz beneath the emitting face 112 without heating central portions of surface layers to a lethal temperature as would otherwise be caused by uniform energy field.

This shaped emitted energy in combination with the central cooling air forced through the applicator enhances the capability of the applicator in heating portions of the tissue, such as malignant masses, located below surface tissue, to lethal temperatures without excessive heating of surface layers than was heretofore possible.

Additionally, the waveguide structure of the applicator 20 is more efficient in carrying electromagnetic energy and coupling the energy into tissue than applicators heretofore available, such as coil, parabolic reflector or paddle type applicators. The applicator 20 operates within its frequency range with an overall efficiency of approximately 98%. That is, if 100 watts of power is applied to the applicator at the connector 158, only two watts are "lost" from the applicator itself, when it is properly coupled to tissue.

Figures 6, 7, 8:
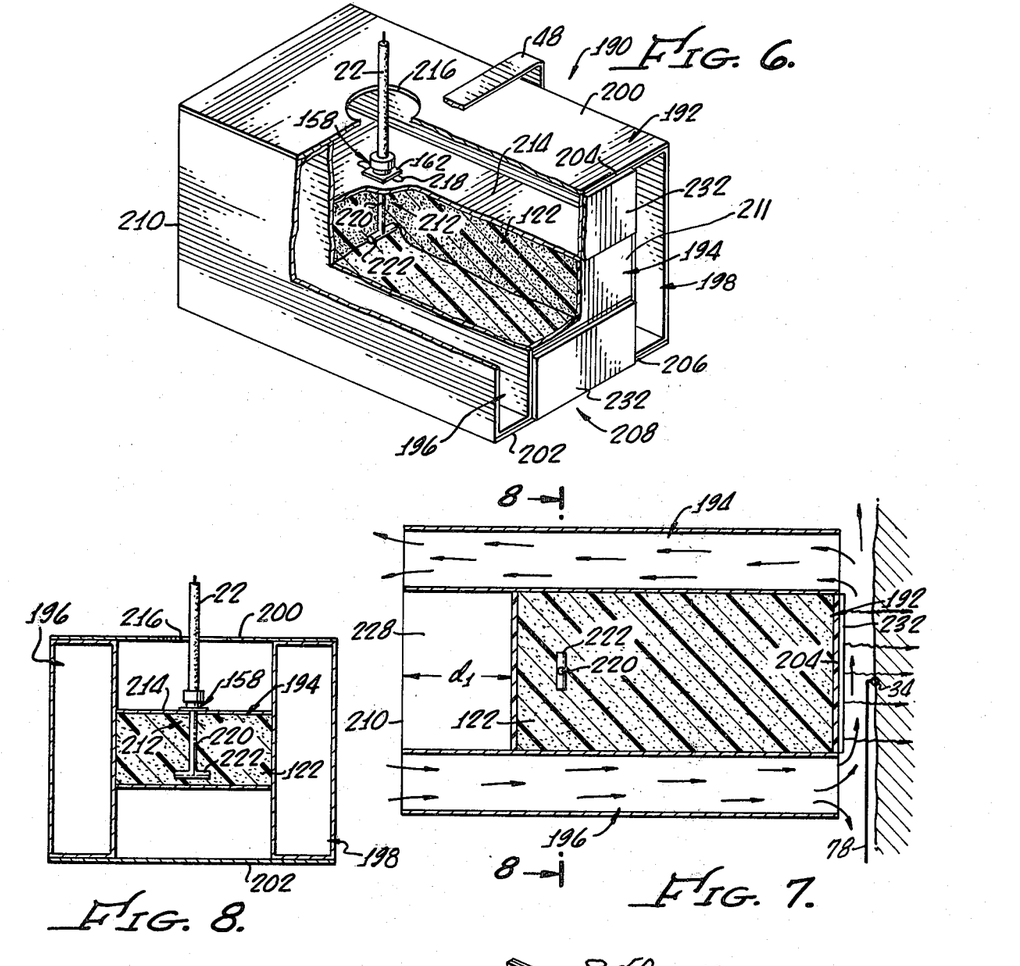
FIG. 6 is an overall perspective view of another embodiment of a waveguide-type transmission line applicator partially broken away to show the dielectric therein, and a coupler for receiving electromagnetic energy from a coaxial cable and for launching the received electromagnetic energy into the waveguide applicator.
FIG. 7 is a cutaway plan view of the applicator of FIG. 6 showing the disposition of dielectric therein and the position of the coupler along with a representation of air flow through the applicator and across the surface of tissue being irradiated; also shown is a representation of a temperature sensor disposed at a surface position on the tissue sample.
FIG. 8 is a cross sectional view taken along line 8—8 of FIG. 7 showing in greater detail the configuration of the waveguide shape and the coupler therein.

Turning now to FIG. 6, there is shown an alternate embodiment of a waveguide-type transmission line applicator 190 for use with the apparatus 10 for irradiating living tissue, or simulations thereof in the frequency range of 200 to 550 MHz. In FIG. 6 like reference numericals identify like components of the applicator 20 shown in FIGS. 2, 3, and 4. Having a lower frequency range than the heretofore discussed applicator 20, the applicator 190 enables deeper penetration of electromagnetic energy, and hence, deeper heating of tissue, or simulations thereof.

In general, the applicator 190 may be classified as a ridged waveguide-type transmission line, and includes a waveguide 192 having a central portion, or channel, 194 and adjoining side portions, or channels, 196, 198. In cross section, the central and side channels 194, 196, 198 form an "H" shape (FIG. 7). The channels, as well as top and bottom panels 200, 202, are constructed of sheet metal, bonded together by soldering, or other fastening means, not shown. Sheet metal plates 204, 206 on an emitting end 208 of the waveguide join the side channels and the central channel. The waveguide central channel 194 is filled with a dielectric medium 122 having a dielectric constant of approximately 12, such as the powder described in connection with the side loaded applicator 20. It is important that the dielectric medium fills the waveguide from the emitting end 208 to a predetermined distance $d_1$, from a rear end 210 of the waveguide. As was discussed in connection with the side wall loaded applicator 20, the dielectric medium, in partially filling the waveguide length, in part enables the waveguide to have a characteristic impedance over a wide frequency range. The ridged waveguide applicator 190 has an operational frequency range of 200 to 550 MHz; the frequency band width ratio being approximately 106%. For the applicator 190, the distance $d_1$, between the dielectric 122 and the rear end 210 may be approximately 3 inches when the overall length of the applicator 190 is approximately 8 inches or greater; the distance, $d_1$, and the length, as well as the height and width of the applicator 190, being determined experimentally using the procedures discussed in connection with the applicator 20.

In addition, it is important to recognize that by loading the central portion 194 of the waveguide with a dielectric medium, essentially all of the electromagnetic energy is transmitted through the dielectric medium, and not through the outer portions 196, 198 of the waveguide. This was pointed out in an article by Gottfried Magerl in *IEEE Transactions of Microwave Theory and Techniques,* Volume MTT-26, No. 6, June, 1978 entitled "Ridged Waveguides Within Homogeneous Dielectric-Slab Loading". Hence, although the overall height and the overall width of the applicator are approximately 4 inches and 5.2 inches respectively, the radiating portion of an emitting face 211 is essentially the height and width of the central portion 194, which are approximately 1.4 and 3.0 inches respectively.

Referring to FIGS. 6, 7 and 8, a coupler, or launcher, 212, including a coaxial type connector 158 mounted to a top plate 214 of the central portion 192 by means of the connector base 162 provides means for receiving electromagnetic energy from the cable 22 and launching such energy into the waveguide applicator. A slot 218 in the top plate 214 enables adjustment of the coupler 212 for optimizing the position of the coupler within the ridged waveguide applicator 190 in accordance with the procedure discussed in connection with the side wall loaded applicator 20. An opening 216 is provided in the top panel 200 to facilitate movement of the coupler 210 within the slot 218.

The coaxial connector center portion 168, not shown in FIGS. 6, 7 and 8, is extended by a rod or pin 220 into the dielectric medium 122. In order to provide proper capacity coupling between the launcher 210 and the waveguide, a T-bar section 222 is attached to the end of the pin 220. As is well known in the art, the exact size and configuration of the pin and T-bar is adjusted to provide proper capacitance coupling being the pin and the waveguide. Other configurations and shapes of couples may be employed with success, but as with the side loaded applicator 20, it is important that the relative placement of the launcher with respect to the dielectric medium 122, and an open portion 228 of the waveguide channel 192, is determined in a manner similar to that discussed in connection with the side loaded applicator 20, to enable the waveguide applicator 190 to operate over a broad frequency range, and at the same time, enable the waveguide to have an average characteristic impedance substantially equal to that of living tissue, or simulations thereof, over the frequency range of 200–550 MHz.

Although the lower operational frequency range of the ridged applicator 190 enables deeper penetration of the electromagnetic energy and the heating of tissue at lower levels, and proportionately less surface heating, cooling of surface tissue may be provided by forcing air through the side portions 194, 196 and across the surface portions of the radiated tissue 12 (FIG. 7). It is to be appreciated that, as discussed in connection with the side loaded applicator 20, other cooling apparatus such as tubing and fluids could be incorporated into the side portions 194, 196 of the applicator as long as such additional apparatus is constructed of materials which have a low dielectric constant and hence would not interfere with the electromagnetic field. For example, a dielectric fluid could be circulated through a dielectric container, such as a bag, not shown, which is placed in the surface of the tissue. In operation, the applicator may be placed in direct contact with the tissue, and the plates 204, 206 may be covered with a dielectric medium 232 to better couple the electromagnetic energy from the applicator into the tissue 12 and to prevent hot spots. Such medium may be solid or fluid, such as water, contained in a pliable plastic bag or the like.

Figure 9:
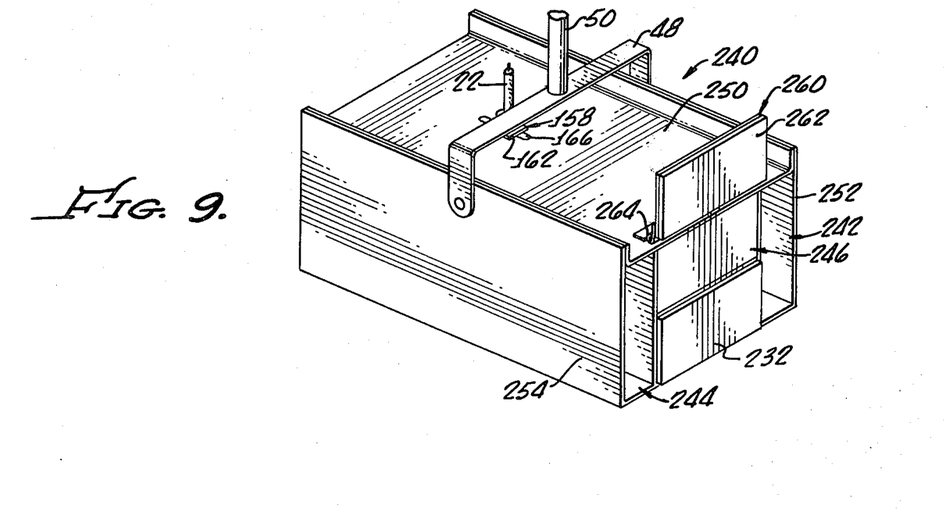
FIG. 9 is an overall perspective view of an alternative embodiment of the applicator shown in FIG. 6 in which a top portion of the applicator of FIG. 6 is electrically represented by a metal flap, in order that the over-all size of the waveguide applicator may be reduced while maintaining approximately the same size radiating area of the applicator shown in FIG. 6; and, FIG. 10 is a plot of a temperature distribution or heating pattern just under the surface of a simulated tissue sample after irradiation thereof with the applicator shown in FIG. 9; the outline of a radiating end of face of the applicator is indicated to show the relative shape of the heating portion with respect thereto.

Referring now to FIG. 9, there is shown another embodiment of a rigid waveguide transmission line applicator 240 similar to the applicator 190, except portions above the center channel 192 have been removed to reduce the overall height of applicator 240. In FIG. 9, like reference numerals identify like components of the applicator 190 shown in FIGS. 6, 7, and 8. The applicator 240 has open side channels 242, 244 and a central channel 246 similar to applicator 190 with the manner of construction being the same. A central channel top plate 250 extends between the outer walls 252, 254 of the side channels. A dielectric medium fills the central portion, as hereinbefore described in connection with applicator 190, and a launcher is placed therein in accordance with the launcher in the applicator 190. All dimensions and details of the dielectric medium, and launcher are substantially the same as those discussed in connection with the applicator 190, but the frequency range is higher. To operate in the 200 to 550 MHz range, the dimensions would change to an overall height and width of 6 inches and 7.7 inches respectively, with height and width of radiating portion of 2 and 4.6 inches respectively.

The upper metal face plate 204 of applicator 190 is replaced by a metal flap 260, for providing an electric simulation of the top portion of the waveguide illustrated as applicator 190. The metal flap may be flexible and covered with dielectric medium 262 to enhance coupling, and by attaching the flap 260 to the top 250 by means of a hinge 264, the flap may be moved and bent so as to conform to various body shapes. This enhances the coupling of the EMR into the body and improves the efficiency of transfer of energy into the body tissue.

In operation, the waveguide 240 performs essentially in the same manner and in the same frequency range as the applicator 190.

Figure 10:
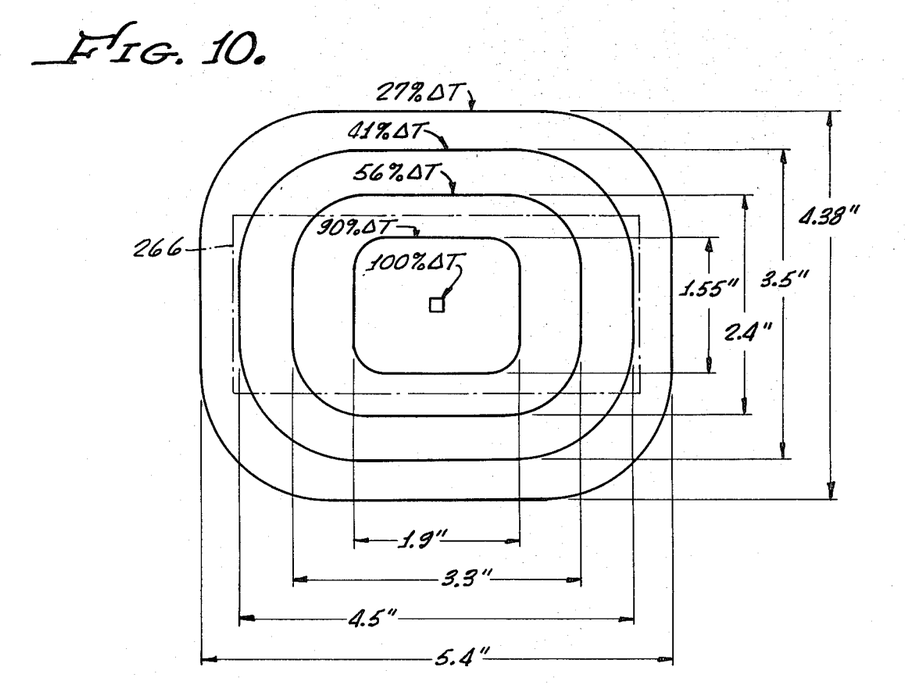

The effectiveness of the applicator 190 in causing heating in a simulated, or phantom, tissue by radiating electromagnetic energy thereinto of approximately 400 MHz is shown in FIG. 10. Plotted are a set of isotherms showing the percent change relative to the greatest temperature change of 100 percent of an area irradiated at 50 watts for a period of less than 20 minutes without surface cooling. Temperatures were measured at a depth of 0.6 cm. below the surface. Shown are isothermal lines for 100 percent, 90 percent, 56 percent, 41 percent and 27 percent of the maximum temperature achieved. Superimposed on the plot is an outline 266 of the central channel of the applicator which has dimensions of approximately 2 by 5 inches.

Figures 11, 13:
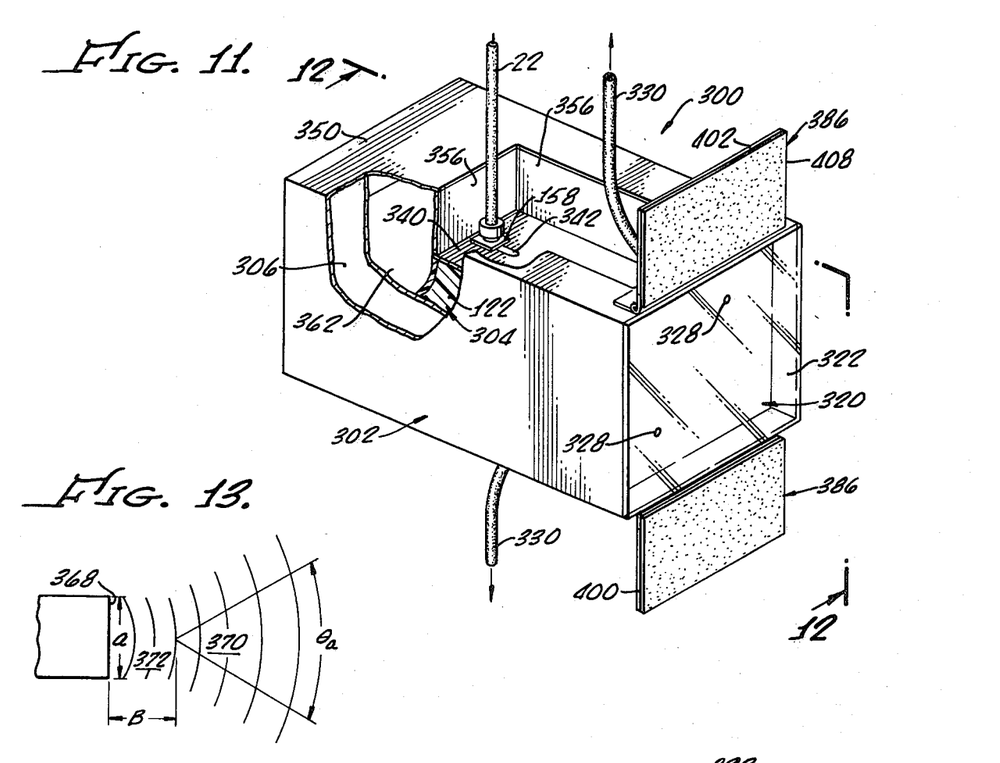
FIG. 11 is an overall perspective view of another embodiment of a waveguide-type transmission line applicator similar to the applicator of FIG. 6 which includes a compartment within the waveguide for containing a second fluid dielectric which may be circulated through the compartment to provide a cooling medium for cooling surface portions of tissue held against the applicator, the second dielectric additionally providing electromagnetic beam collimation, the applicator being partially broken away to show the disposition of a first dielectric therein.
FIG. 13 is a diagram of electromagnetic energy radiated from a radiating surface showing the relative divergence of electromagnetic energy within near and far field areas from said radiating surface.

Turning now to FIG. 11, there is shown still another embodiment of a waveguide type transmission line applicator 300 for use with the apparatus 10, or separately, for irradiating living tissue, or simulations thereof, in a frequency range of approximately 200 to 800 MHz. In FIG. 11, like reference of numerals identify like components of the applicator 190, shown in FIGS. 6, 7 and 8.

The applicator 300 of FIG. 11, is similar to the applicator 190 having approximately the same overall dimensions and including a waveguide 302 with a central portion, or channel 304, and adjoining side portions, or channels, 306.

Figure 12:
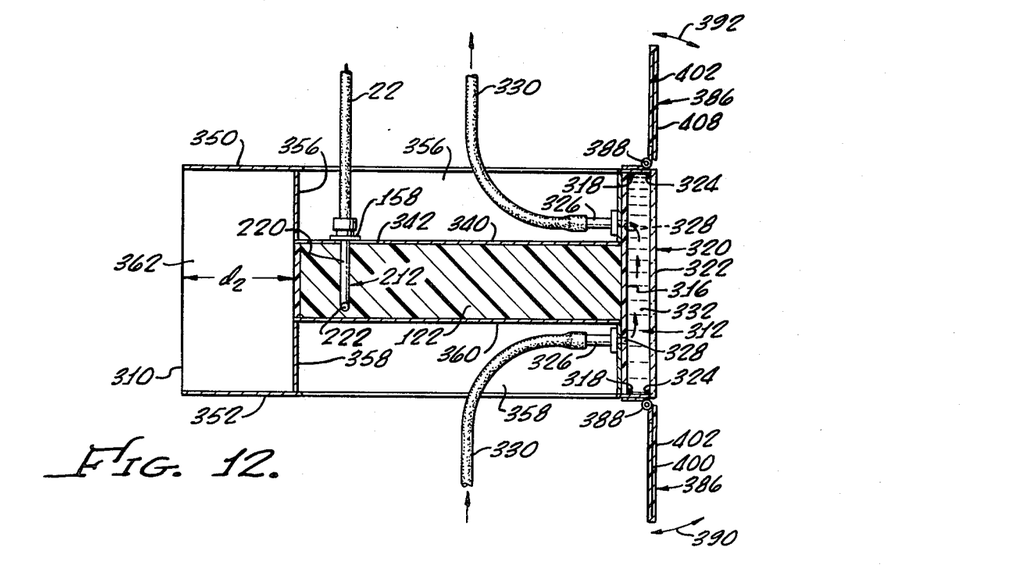
FIG. 12 is a cross sectional view of the applicator of FIG. 11 taken along line 12—12 showing the disposition of a coupler and the dielectrics therein.

As more clearly shown in FIG. 12, the waveguide central channel 304 extends from a predetermined distance, $d_2$, from a rear end 310 of the waveguide 302 to a compartment 312 disposed within the waveguide at a forward end 314 thereof.

The channel 304 is filled with a first dielectric medium 122 having a dielectric constant of 12, such as the powder described in connection with the side loaded applicator 20. The channel 304 adjoins a back plate 316 of the compartment 312 which consists of a low dielectric material, such as Plexiglas, which may be sealed to the waveguide 302 with an appropriate glue, or caulking compound, 318.

The compartment 312 has a forward wall 320 forming an applicator radiating surface 322, the wall being formed from a material such as glass which has a relatively high thermal conductivity, as compared to Plexiglas for example, and sealed to the waveguide 302 with an appropriate glue, or caulking compound, 324.

A pair of fittings 326 secured through a pair of holes 328 in the Plexiglas wall 316, and connected to tubing 330, enables a second dielectric medium, or fluid, 332 to be pumped, or circulated, through the compartment, the second dielectric acting as a cooling medium for cooling the applicator radiating surface 324 and surface portions of living tissue, not shown, during radiation thereof when the tissue is held against the applicator radiating surface.

Distilled water, which has a dielectric constant of approximately 70 to 80, may be used as the fluid dielectric, 332. Although other fluid dielectric mediums may be used which may have a dielectric constant of approximately 20 to 100, distilled water is preferred because of its availability, cost, and ease in handling. It should be appreciated that the dielectric mediums 122 and 322 partially fill the waveguide 302 which enables the waveguide applicator 300 to have a characteristic impedance, over the frequency range of 200 to 800 MHz, of approximately 50.

As was discussed in connection with FIG. 6, a coupler 212, including a coaxial type connector 158 mounted to top plate 340 of the central channel 304 is provided for receiving electromagnetic energy from the cable 22 and launching such energy into the waveguide applicator 300. As discussed in connection with the applicator 190, a slot 342 may be provided in the central channel top plate 340 to enable the adjustment of the coupler 212 to optimize the position of the coupler within the ridged waveguide applicator 300 in accordance with the procedure hereinbefore outlined.

A waveguide top plate 350 and bottom plate 352 are interconnected with the central channel top plate 340 and a central channel bottom plate 354, respectively, by upstanding walls 356, 358. This configuration enables the coupler 212 to be mounted directly onto the central channel top plate 340 and further enables ready access to the rear compartment wall 316 in order to facilitate attachment of the fittings 326 thereto.

As hereinabove discussed in connection with the applicator 190, the coupler connector center portion 168, not shown in FIGS. 11 and 12, is extended by a rod, or pin, 220 into the dielectric medium 122. In order to provide proper capacitive coupling between the launcher 210 and the waveguide, a T bar section 222 is attached to the end of the pin 220.

It is important that the location of the launcher with respect to the dielectric medium 122 and an open portion 362 of the waveguide 302, is determined in a manner similar to that discussed in connection with the side loaded applicator 20, and the ridged applicator 190, in order to enable the waveguide applicator 300, to operate over the frequency range of 200 to 800 MHz, and at the same time, enable the waveguide to have an average characteristic impedance substantially equal to that of living tissue, or simulations thereof.

A feature of the embodiment of the present invention as shown in FIGS. 11 and 12 is the fact that the fluid dielectric 332 also acts as a collimator for electromagnetic energy radiated from the applicator irradiating surface 322. Additionally, a larger radiation surface 322, may be provided, as compared with the radiating surface 211, of the applicator 190, for irradiating a larger surface as may be desired for larger malignant growths.

In order to achieve this collimating effect, the compartment 312, as well as the fluid dielectric 332 must be contained within the waveguide 302. The electromagnetic energy conducted by the dielectric 122 in the central channel 304, is coupled into the fluid dielectric 322 through the Plexiglas back plate 316, and is conducted, or propagated, throughout the fluid dielectric 332 and emitted from the radiating surface 322. The electromagnetic lines of force, not shown, are redistributed by the fluid dielectric 332, so as to spread throughout the fluid dielectric and across the radiating surface 322. The dominate mode of electromagnetic energy which propagates within the fluid dielectric is the $TE_{1,0}$ mode, as described, for example in, "Reference Data for Radio Engineers", 5th Ed., Published by ITT, 1970.

Although the fluid dielectric 332 may be a lossy medium, only a relatively short length, compared to the length of the central channel 304, is necessary to redistribute, or spread the electromagnetic energy to a greater area for emission from the radiating surface 322. The larger area enables a greater collimation of the emitted electromagnetic energy.

In general, as electromagnetic energy, radiated from a surface 368, (FIG. 13) penetrates a lossy medium, such as living tissue, divergence, in accordance with the well known formula $1/r^2$, where r is the distance from the surface 368 does not occur until the radiated energy reaches a certain distance, B, from the radiating surface (FIG. 13). The area beyond the distance B is known as the far field region 320, the area between the distance B and the radiating surface 368 being known as the near field region 372.

In the near field region 372, the emitted electromagnetic energy, as represented by the lines 374 do not diverge significantly as they move away from the radiating surface 368 until they reach the distance B in front of the radiating surface. At that point the electromagnetic energy, as represented by the lines 376 begin to diverge in accordance to the $1/r^2$ formula. The divergence angle from the point B forward of the applicator is approximately $\theta_a$ where, $\theta_a$ is approximately $$\theta_a \simeq 64.45 \frac{\lambda_m}{a}$$

$\lambda_m$ being the wavelength of the radiated electromagnetic energy in tissue and a being a dimension of the radiation surface (FIG. 13).

The boundary B, between the near field and the far field regions is known to be approximately, $$B = A/2\lambda_m \text{ (where A = aperature area)}$$

It is to be appreciated that electromagnetic energy beam divergence is dependent upon the area of the radiating surface 368, the one dimensional analysis described herein being chosen for clarity. As an example, if characteristic dimensions of applicator 300 are 10 inches deep, 4 inches high, 5 inches wide with an internal dielectric channel of 1.5 inches high and 3 inches assuming the fluid chamber were removed, the radiating surface would be 1.5 by 3.0 inches. At a frequency of 433 MHz, the wave length radiated into living tissue or simulations thereof is approximately 8.76 centimeters, which the boundary distance B, being approximately 0.65 inches, and the angle of divergence $\theta_a$ being approximately 148° in the vertical plane as shown in FIG. 13, and 74° in a perpendicular or horizontal plane, not shown.

Comparing now the increased radiating size of applicator 300, the comparative dimensions is A equal to 4×5 inches, hence at 433 MHz, B would be approximately 2.9 inches with $\theta_a$ equal to approximately 50°, hence collimation is obtained to approximately 2.9 inches, or 7.4 centimeters with a divergence angle of only approximately 50° beyond this point.

Coupling of electromagnetic energy between the applicator 300 and living tissue, not shown in FIGS. 11 and 12, may be further enhanced by means of a pair of adjustable flaps 386, mounted to the waveguide 302 by hinges 388. The hinges enable the flaps to be moved in the directions indicated by arrows 390, 392, so as to conform to tissue portions, not shown, which may extend beyond the waveguide forward end 314.

The flaps are preferably constructed of metallic substance 400, 402, and may be flexible, to improve the efficiency of energy transfer into body tissue, not shown.

A dielectric coating or medium 408 may be applied to the flaps 386 in order to further enhance energy coupling, and prevent hot spoting. It should be appreciated that the applicator 300 may be constructed, in accordance with this invention, in various sizes with the range of radiated frequencies being lower as the dimensions of the applicator are increased, or higher as the dimensions are decreased.

Figure 14:
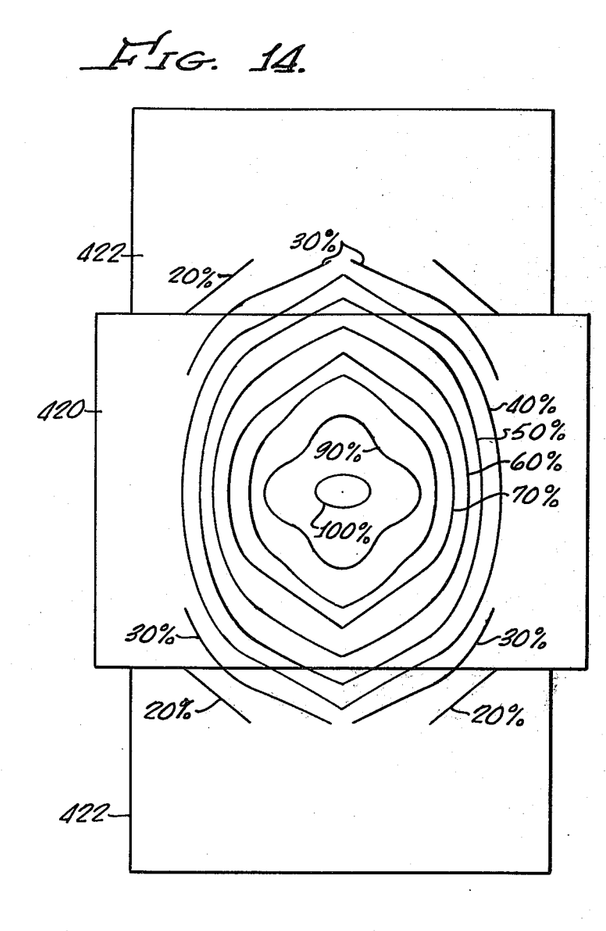
FIG. 14 is a plot of a temperature distribution or heating pattern approximately one centimeter below the surface of a simulated tissue sample after irradiation thereof with the applicator shown in FIG. 11, the outline of a radiating end of face of the applicator is indicated to show the relative shape of the heating portion with respect thereto; and, FIG. 15 is a plot of a temperature distribution or heating pattern approximately four centimeters below the surface of a simulated tissue sample after irradiation thereof with the applicator shown in FIG. 11, the outline of a radiating end of face of the applicator is indicated to show the relative shape of the heating portion with respect thereto.
Figure 15:
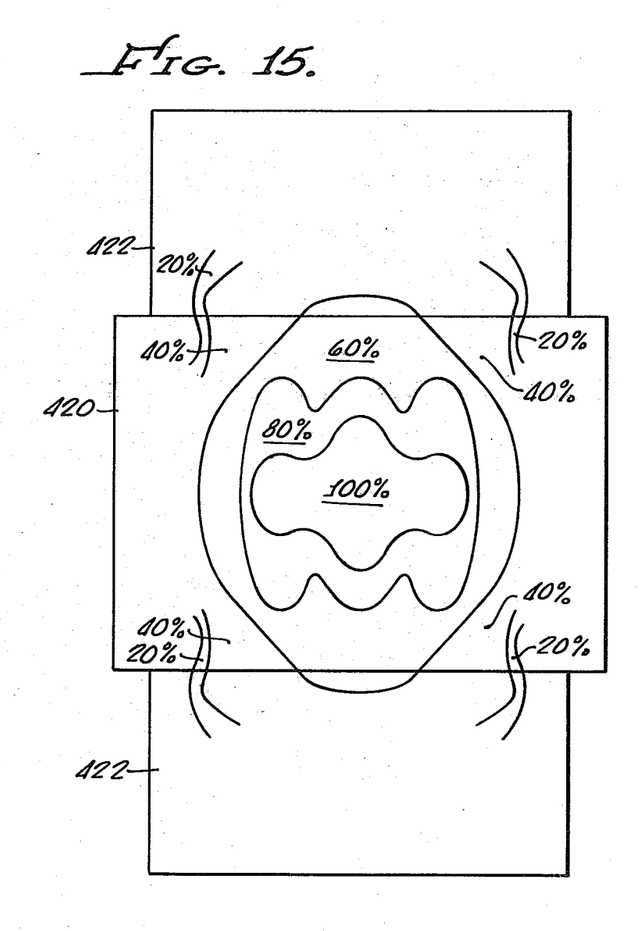

The effectiveness of the applicator 300 causing heating in simulated, or phantom tissue, by radiating electromagnetic energy thereinto at approximately 300 MHz is shown in the FIGS. 14 and 15. Plotted in these Figures is a set of isotherms showing the percent of change relative to the greatest temperature change of 100% of an area radiated at a power of approximately 50 watts with cooling dielectric fluid 332 flowing through the compartment 312 at approximately one gallon per minute. The temperature of the fluid dielectric was thermostatically controlled to between 5° and 10° centigrade.

FIG. 14 shows isotherms taken at a distance of 1 centimeter into the radiated phantom material, from the irradiating surface, and FIG. 15 shows isotherms at a distance of 4 centimeters from the radiating surface. Isotherm lines are shown for various percentages, as indicated on the drawings, of the maximum temperature achieved at the indicated depth of 1 centimeter or 4 centimeters. Superimposed on the plots are an outline 420 of the radiating surface 324 along with an outline 422 of the flaps 386.

Comparing FIGS. 14 and 15 with FIG. 10, it can be seen that the use of the fluid dielectric for spreading and collimating the emitted radiation is effective in causing a larger area, within the irradiated sample, to be heated.

It is to be appreciated that the plots shown in FIGS. 14 and 15 are based on experimental measurement, and that discontinuities and ripple-like variations therein, are attributed to experimental error.

Although there has been described above particular arrangements of an apparatus for irradiating living tissue, or simulations thereof, in accordance with the invention for the purpose of illustrating the manner in which the invention may be used to advantage, it will be appreciated that the invention is not limited thereto. Accordingly, any and all modifications, variations or equivalent arrangements which may occur to those skilled in the art, should be considered to be within the scope of the invention as defined in the appended claims.

What is claimed is:

1. An applicator for irradiating electromagnetic energy into living tissue, or simulations thereof for causing hyperthermia therein, comprising:
  (a) a waveguide-type transmission line having electrically conductive top, bottom and side walls, and a radiation emitting face and an opposite rearward face;
  (b) dielectric means disposed in the transmission line for enabling the transmission line to have a characteristic impedance, when radiating electromagnetic energy into the tissue, or simulations thereof, within a preselected frequency range having a preselected bandwidth ratio, approximately matching an average characteristic impedance of the living tissue, or simulations thereof, in said preselected frequency range, said dielectric means including a portion extending rearwardly from said radiation emitting face towards said rearward face and for a distance, L, which is less than length of said transmission line; and,
  (c) coupling means configured for receiving said electromagnetic energy from a conductor connected to a radiation source and for launching the electromagnetic energy into the transmission line for irradiation thereby into tissue or simulations thereof;
    said coupling means including a radiation energy coupler disposed through one of said transmission line walls into said portion at an axial position adjacent a rearward end thereof.

2. The applicator according to claim 1, including means for cooling surface portions of the tissue, or simulations thereof, during irradiation of said tissue or simulations thereof by said applicator.

3. The applicator of claim 2 wherein the cooling means includes at least one air circulation passage within the applicator means for forcing air through said passage and across the surface portions of the tissue, or simulations thereof.

4. The applicator according to claim 1, wherein the dielectric means dielectric portion is rectangular and extends between the transmission line top and bottom walls, wherein the dielectric length L is equal to at least one-third of wavelengths associated with said preselected frequency range and wherein the dielectric length L is less than about twice a distance, d, between the rearward end of said dielectric portion and the rearward face of said transmission line.

5. The applicator according to claim 1, wherein said dielectric portion has a dielectric constant greater than about 10.

6. The applicator according to claim 9, wherein said preselected bandwidth ratio is in at least 30%.

7. An applicator according to claim 1 wherein said waveguide-type transmission line has at least one adjoining open side portion coupled to said dielectric portion; and
  further comprising cooling means for forcing air through said side portion and out of a forward end of said transmission line, thereby cooling surface portions of the living tissue, or simulations thereof, when the transmission line is disposed in an operative relationship therewith.

8. An applicator for irradiating electromagnetic energy into living tissue, or simulations thereof, for causing hyperthermia therein, comprising:
 (a) a waveguide-type transmission line having electrically conductive top, bottom and side walls and a radiation emitting face and an opposite rearward face;
 (b) dielectric means disposed in the transmission line for enabling the transmission line to have a characteristic impedance, when radiating electromagnetic energy into the tissue, or simulations thereof, within a preselected frequency range having a preselected bandwidth ratio, approximately equal to an average characteristic impedance of the living tissue, or simulations thereof, in said preselected frequency range;
 said dielectric means including a dielectric portion which has a forward surface spaced rearwardly of said transmission line emitting face and which has a rearward surface spaced forwardly from said transmission line rearward face;
 (c) coupling means configured for receiving said electromagnetic energy from a coaxial type conductor connected to a radiation source and for launching the electromagnetic energy into the transmission line for irradiation thereby into tissue or simulations thereof; and,
 (d) means for cooling surface portions of the tissue or simulations thereof during irradiation, said cooling means being disposed forwardly adjacent to said surface of said dielectric portion.

9. The applicator of claim 8 wherein the cooling means forms part of said dielectric means and includes a fluid dielectric and a compartment for containing the fluid dielectric, said compartment being disposed across the transmission line between the forward surface of the dielectric portion and the radiation emitting face thereof, said compartment having a wall forming an applicator radiating surface and including fluid inlet and outlet means for enabling the fluid dielectric to be circulated through the compartment, thereby enabling the fluid dielectric to act as a cooling medium for cooling surface portions of the tissue or tissue simulating material during irradiation thereof by the applicator when the applicator radiating surface is held against a surface of said tissue or tissue simulating material.

10. The applicator according to claim 9 wherein the fluid dielectric is disposed in an operative relationship with the dielectric portion and the waveguide-type transmission line for collimating the electromagnetic energy radiated from said applicator.

11. The applicator according to claim 9 wherein the fluid dielectric has a greater dielectric constant then that of said dielectric portion.

12. The application according to claim 8, wherein the coupling means includes a radiation energy coupler disposed through one of said transmission line walls into said dielectric portion, at an axial position adjacent to said rearward surface thereof and configured for receiving electromagnetic energy from a coaxial-type conductor and for launching the electromagnetic energy into the waveguide-type transmission line without electromagnetic energy reflecting back into the coaxial conductor throughout said preselected frequency range.

13. The applicator according to claim 8, wherein said frequency range has a bandwidth ratio in excess of unity.

14. The applicator according to claims 1 or 8 further including a moveable member attached to said transmission line adjacent said radiating face for enabling enhanced electromagnetic energy coupling with differently shaped tissue bodies when the applicator is placed in an operative relationship with tissue or simulations thereof to be irradiated and said moveable member is moved to conform to a radiation receiving surface of said tissue or tissue simulations.

* * * * *